United States Patent
Klingenbeck-Regn

(10) Patent No.: US 8,254,655 B2
(45) Date of Patent: Aug. 28, 2012

(54) METHOD FOR TEMPORALLY REGISTERING IMAGE SERIES DATASETS

(75) Inventor: Klaus Klingenbeck-Regn, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 904 days.

(21) Appl. No.: 12/319,518

(22) Filed: Jan. 8, 2009

(65) Prior Publication Data

US 2009/0185728 A1    Jul. 23, 2009

(30) Foreign Application Priority Data

Jan. 18, 2008    (DE) .................. 10 2008 005 071

(51) Int. Cl.
*G06K 9/00*    (2006.01)
*G06K 9/62*    (2006.01)

(52) U.S. Cl. ....................... 382/131; 382/224

(58) Field of Classification Search .......... 382/128–132, 382/224, 294; 600/407; 715/764

See application file for complete search history.

(56) References Cited

U.S. PATENT DOCUMENTS

| | | | |
|---|---|---|---|
| 2005/0025357 A1* | 2/2005 | Landwehr et al. | 382/170 |
| 2006/0245660 A1* | 11/2006 | Hung | 382/254 |
| 2007/0088209 A1* | 4/2007 | Lotjonen | 600/407 |
| 2007/0167784 A1 | 7/2007 | Castro-Pareja | |
| 2008/0265166 A1* | 10/2008 | Shekhar et al. | 250/363.03 |
| 2008/0285819 A1* | 11/2008 | Konofagou et al. | 382/128 |

FOREIGN PATENT DOCUMENTS

| | | |
|---|---|---|
| DE | 102005037426 A1 | 2/2007 |
| EP | 1209622 B1 | 7/2006 |
| WO | WO 2005046473 A1 | 5/2005 |

* cited by examiner

*Primary Examiner* — Vu Le
*Assistant Examiner* — Amara Abdi

(57) ABSTRACT

A method for temporally registering two image series datasets, each of which images a preferably periodically moving object and consists of time-resolved single images each composed of pixels or voxels, with a single image, recorded at a first instant, in the first image series dataset being in each case assigned to a single image, recorded at the same or another instant, in the second image series dataset, with the specific single image in the second image series dataset exhibiting maximum similarity to the single image in the first image series dataset being determined for registering a single image in the first image series dataset.

17 Claims, 3 Drawing Sheets

METHOD FOR TEMPORALLY REGISTERING IMAGE SERIES DATASETS

CROSS REFERENCE TO RELATED APPLICATIONS

This application claims priority of German application No. 10 2008 005 071.7 filed Jan. 18, 2008, which is incorporated by reference herein in its entirety.

FIELD OF THE INVENTION

The invention relates to a method for temporally registering two image series datasets, each of which images a preferably periodically moving object and consists of time-resolved single images each composed of pixels or voxels, with a single image, recorded at a first instant, in the first image series dataset being in each case assigned to a single image, recorded at the same or another instant, in the second image series dataset.

BACKGROUND OF THE INVENTION

Biosignals are mostly used for registering image datasets of moving objects. A known instance thereof in the case of a living thing is the ECG signal. The image series datasets can therein derive from an imaging modality at different instants, they can have been recorded based on a plurality of imaging modalities at the same instant, or they can derive from different modalities at different instants. Image datasets containing a plurality of single images recorded at different instants within the periodic motion will be referred to below as image series datasets. However, a prerequisite for the use of biosignals for temporal registration is that the frequency of the biosignal does not change between measuring instants. If it does, as in the case of, for instance, cardiac arrhythmia, the result will be a misregistration of the image series datasets. It will hence not be possible to assign instants of the biosignal at a first examination instant one-to-one to the instants of the biosignal at a second examination instant.

SUMMARY OF THE INVENTION

The problem underlying the invention is hence to disclose a temporal registration method that can be performed independently of biosignals.

For resolving said problem it is inventively provided in a method of the type cited in the introduction for the specific single image in the second image series dataset exhibiting maximum similarity to the single image in the first image series dataset to be determined for the purpose of registering a single image in the first image series dataset.

A temporal registration method of said type will enable registering that is independent of biosignals. Possible errors due to changes in the frequency of the periodic motion will be avoided thereby in registering.

The first image series dataset preferably has one temporal dimension, two or three spatial dimensions, and possibly at least one further dimension that is in particular dependent on arbitrary recording parameters. This variable mode of image data creation will make it possible always to select the most advantageous parameters for image recording for the image series dataset. With a higher temporal resolution, for example, the spatial dimensions can be restricted to two in number; three spatial dimensions can be recorded to achieve a higher spatial resolution, although that will typically be at the expense of a lower temporal resolution. Further dimensions are, though, also conceivable alongside those. For example in the case of nuclear spin tomography recordings a T1 weighting or quantifying, a T2 weighting or quantifying, or a diffusion weighting or quantifying can be provided as further conceivable dimensions. Alongside these there are further parameters such as flux, MTC (Magnetization Transfer Contrast), and perfusion. This is not a definitive list; any possible parameter can serve as a further dimension. It is, however, customary for reasons of time to limit oneself to the parameter that will yield the most information for the matter in hand. Nuclear spin tomography is also to be regarded only as an instance of an imaging modality; further imaging modalities such as x-raying, computed tomography, ultrasound, and PET (Positron Emission Tomography) are likewise possible. This list, too, is to be regarded not as definitive but only as exemplary.

The second image series dataset can expediently have one temporal dimension, two or three spatial dimensions, and possibly at least one further dimension that is in particular dependent on arbitrary recording parameters. All the possibilities available for recording the first image series dataset will be available also for the second image series dataset. The second image series dataset will, though, be totally independent of the first in that all kinds of dimensions, which is to say temporal, spatial, and any other dimensions, can mutually differ in terms of their number and resolution. Thus, if the first image series dataset has, for example, two spatial dimensions, then the second image series dataset can likewise have two spatial dimensions or possibly even three.

A spatially higher-dimensional image series dataset can advantageously be back-projected onto the spatial dimensions of the spatially lower-dimensional image series dataset. A maximum similarity between a single image in the first image series dataset and the single images in the second image series dataset will be made easier to detect owing to that process. If the single images in the first image series dataset have, for example, two spatial dimensions—which case is referred to typically as a series of 2D images—and the single images in the second image series dataset have three spatial dimensions—which images are referred to typically as 3D images—, then projecting the 3D images in the second image series dataset back onto 2D images will simplify the use of known algorithms for detecting maximum similarity. Algorithms of such kind are usually provided for equidimensional datasets.

Maximum similarity to each single image in the second image series dataset can expediently be calculated for one or for every single image in the first image series dataset. In that way it will be ensured that for each single image in the first image series dataset the specific single image in the second image series dataset to which it exhibits maximum similarity will be detected.

Maximum similarity to single images in the second image series dataset can advantageously be calculated for one or for every single image in the first image series dataset within a temporally limited range. A computing time optimization will be achieved through the limitation to a comparison of the single image in the first image series dataset with a few single images in the second image series dataset. It is expediently possible for the temporal sequence of the respective single images not to vary. This means that if a single image in the first image series dataset is to be assigned to an instant in the second period half, then a single image in the second image series dataset, which image is likewise to be assigned to the second period half of the periodic motion, will not be able to undergo meaningful assignment to a single image in the first image series dataset if maximum similarity to single images in the first image series dataset from the first period half is also determined. Assigning to the individual sections of the instants of the periodic motion could be done, for example, by recording biosignals, but that data is used only for presorting.

A distance measure that is a measure of difference between two single images can expediently be used as a measure of maximum similarity. In this case it holds that the dissimilarity will be the greater, the greater the numeric value of the distance measure is and, conversely, the similarity of the compared single images will be the greater, the smaller the numeric value of the distance measure is. Multifarious options known from mathematics are available for calculating the distance measures.

A distance function that is a measure of the distance between two paired pixels or voxels of the single images, requiring to be assigned, in the image series datasets can expediently be used for calculating the distance measure. The distance function therefore determines how the numeric values of the paired pixels of the single images are mutually linked for calculating the distance measure. A multiplicity of known options already exist for distance functions also.

The Euclidean distance can expediently be used as the distance function. Said distance function has proved particularly advantageous for use in metric spaces. The Euclidean distance is formed as the root of the sum of squares of the individual numeric values.

The Manhattan distance can alternatively be used as the distance function. The Manhattan distance is defined as the sum of amounts of the numeric values of the paired pixels of the single images requiring to be compared. It can be calculated very easily and very quickly.

It is, though, generally possible to use any distance function provided it is only monotonic. This means that the numeric value it yields has to increase in size when the distance between the numeric values of the paired pixels becomes greater, and vice versa.

By calculating the distance function a numeric value whose size depends on the distance function employed is therefore obtained in each case for the paired pixels of the images requiring to be compared. Said values produced by the distance function then have to be mutually linked. This is the function of the distance measure. The information contained in the numeric values produced by the distance function is therefore, so to speak, aggregated at a higher level by the distance measure.

The sum of all numeric values obtained by means of the distance function can expediently be used for calculating the distance measure. Summation is therein a simple, arithmetic operation that is economical in terms of computing time. The greater the distance measure obtained thereby is, the more dissimilar the compared images will be.

The root of the sum of squares of all the numeric values obtained by means of the distance function can alternatively be used for calculating the distance measure. Using the sum of squares will weight large numeric values higher than small ones, as a result of which a large difference between individual pixels of the single images will be weighted higher than general, small differences.

Mutual information can expediently be used for calculating maximum similarity. Mutual information is a measure of the distance between two distributions. This registration measure known from the domain of statistics is based on calculating relative entropies. The numeric values of the pixels of the single images are therein interpreted in each case as being random variables. The mutual information is at its maximum in the event of complete dependency of the random variables, which is to say if the images tally. Embodiments for calculating the mutual information of two single images for identical imaging modalities or for different imaging modalities are sufficiently known.

Maximum similarity can be determined with reference to at least one freely definable image region. What is achieved thereby is that those image regions that are the most informative as regards similarity will be used by preference for determining maximum similarity. For example in x-ray images the contrast for soft-part tissue is low. Were images having large portions of soft-part tissue then to be compared, then said tissue containing little information would, although neither expedient nor desirable, be included in the calculation of maximum similarity having a very high weighting.

An anatomical landmark, in particular coronaries or bones, can advantageously be used as the image region. Through using anatomical landmarks as image regions requiring to be compared, those image regions will be selected that are highly informative in terms of similarity between the single images requiring to be compared. A medical instrument shown in the image can be used as a possible further image region. An instrument of said kind is typically readily distinguishable from the tissue being examined and will appear in the image region in at most low numbers but usually once only. It is therefore excellently suited for registering the single images with one another.

BRIEF DESCRIPTION OF THE DRAWINGS

Further advantages, features and specifics of the invention will emerge from the exemplary embodiments described below and with reference to the drawings, in which.

DETAILED DESCRIPTION OF THE INVENTION

Figure 3:
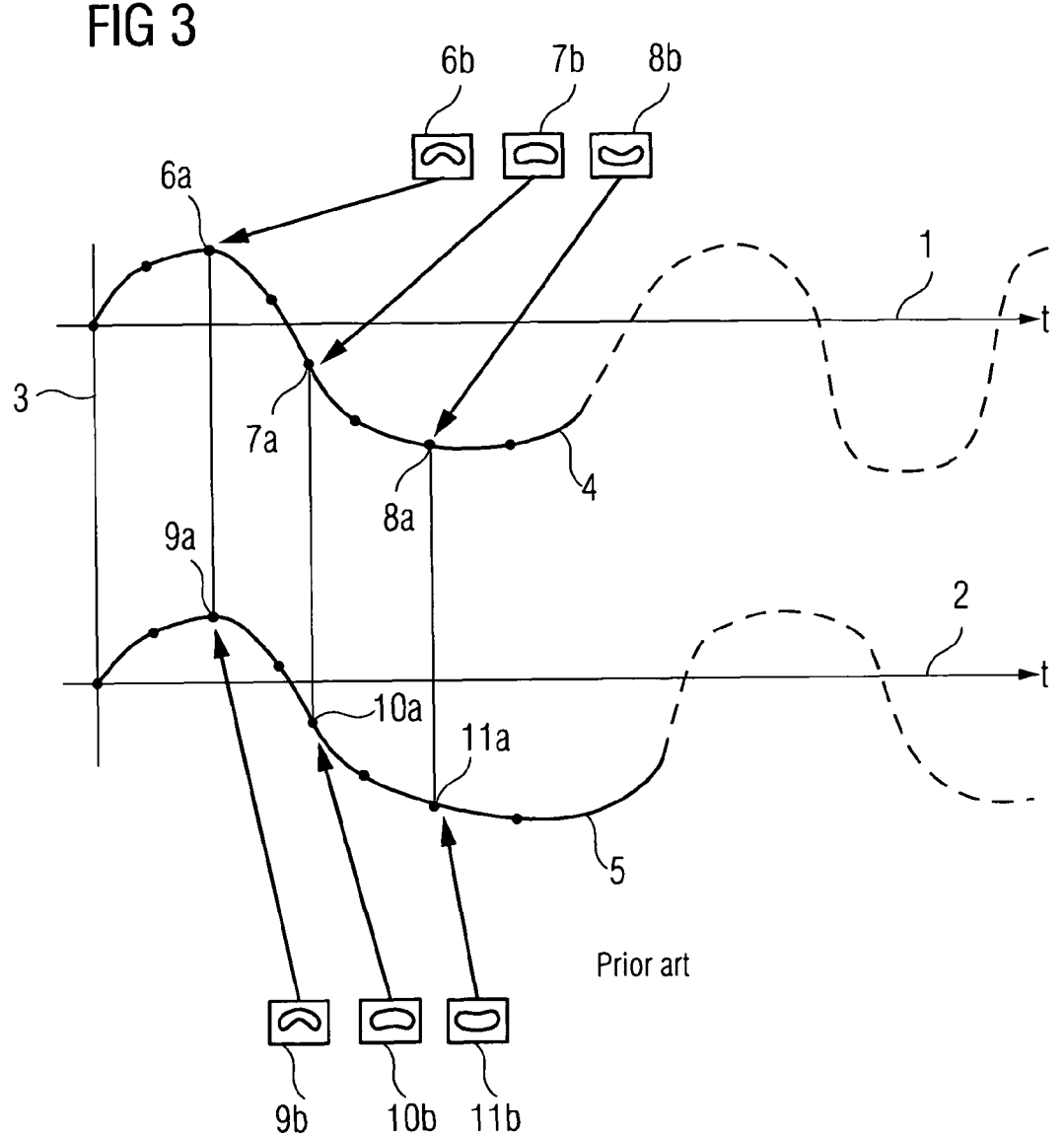
FIG. 3 is a schematic of temporal registering of two image series datasets according to the prior art.

FIG. 3 is a schematic of a method for temporally registering two image series datasets according to the prior art. The curve of an ECG signal 4 at a first examination instant is plotted above the time axis 1. The zero point of the periodic motion is indicated by the line 3. The single images 6b, 7b, and 8b in the first image series dataset are assigned to instants, determined by recording of the ECG signal, of the periodic motion. The instants 6a, 7a, and 8a established by means of the ECG have been plotted on the curve 4. In comparison therewith, what can be seen on the time axis 2 is the curve 5 of an ECG signal at a second examination instant with the corresponding instants 9a, 10a, and 11a and single images 9b, 10b, and 11b assigned thereto. As can be seen, the frequency of the signal curve of the periodically moving object has changed, as a result of which the single images that are similarly temporally distanced from the line 3 indicating the zero point no longer correspond to the same motion conditions. While the information relating to the images 6b and 9b will still very largely mutually correspond at the start of the periodic motion, similarity will become greater with increasing temporal distance from the zero point on account of the change in frequency. Although the instants 8a and 11a are at the same distance from the zero-point line 3 of the periodic motion, the images 8b and 11b no longer reflect the same motion condition. Temporal registering by means of the biosignal will hence have an erroneous outcome.

Figure 1:
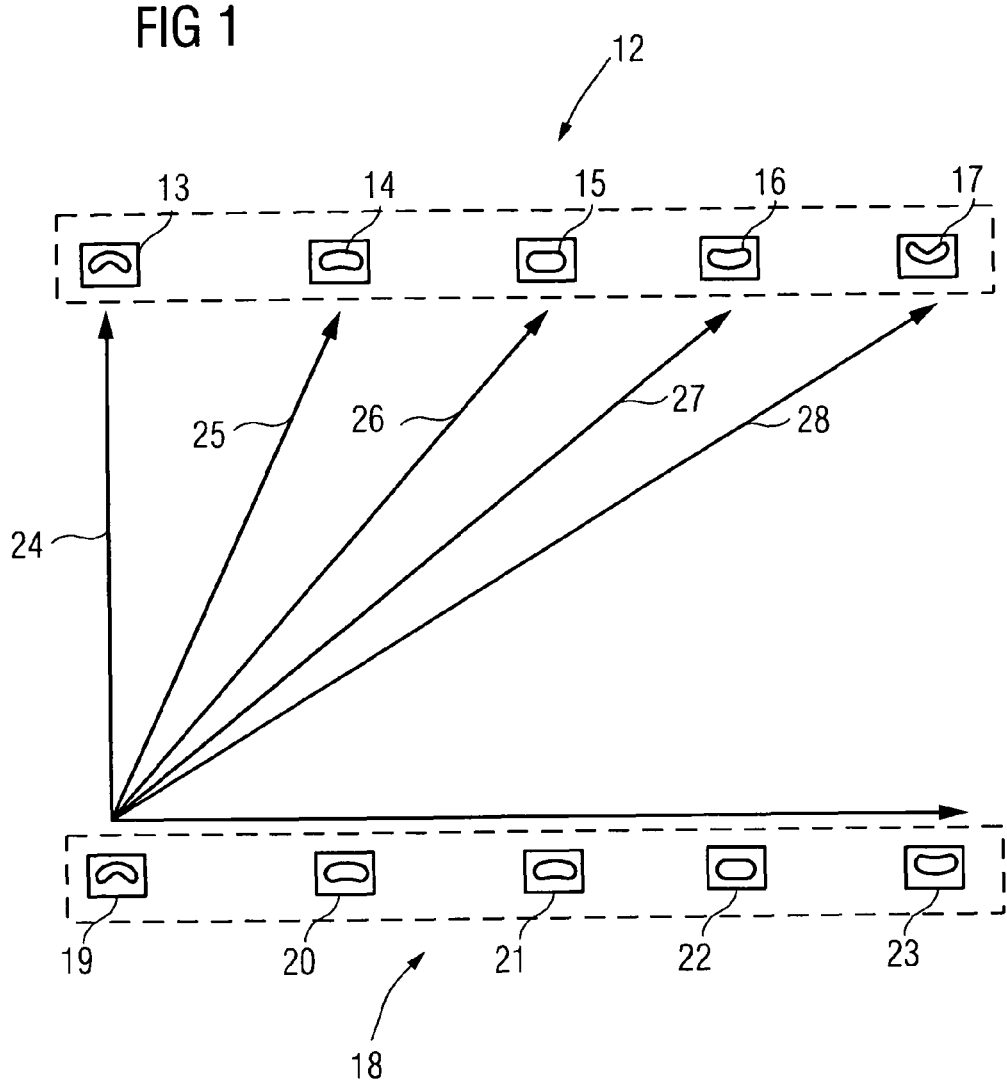
FIG. 1 is a schematic of an inventive method in a first embodiment variant.

FIG. 1, by contrast, is a schematic of the inventive method in a first embodiment variant. What is shown is a first image series dataset 12 that was recorded at a first examination instant and contains the single images 13, 14, 15, 16, and 17. The sequence of the position of the instants within the periodic motion therein corresponds to the sequence shown, which is to say that the image 13 is closest to the zero point of the periodic motion. The second image series dataset 18 containing the single images 19, 20, 21, 22, and 23 is also shown correspondingly. A single image in the second image series dataset 18 is, though, no longer assigned via a biosignal but based on consideration of the similarities 24, 25, 26, 27, and 28 between the first single image 19 in the second image series dataset 18 and each single image 13, 14, 15, 16, and 17 in the first image series dataset 12. Said consideration is applied also to the further images 20, 21, 22, and 23 in the second image series dataset 18. Temporal misregistration will no longer occur because it is no longer a distance from the zero point of the periodic motion that is decisive but, instead, similarity to the single images in the first image series dataset 12.

Figure 2:
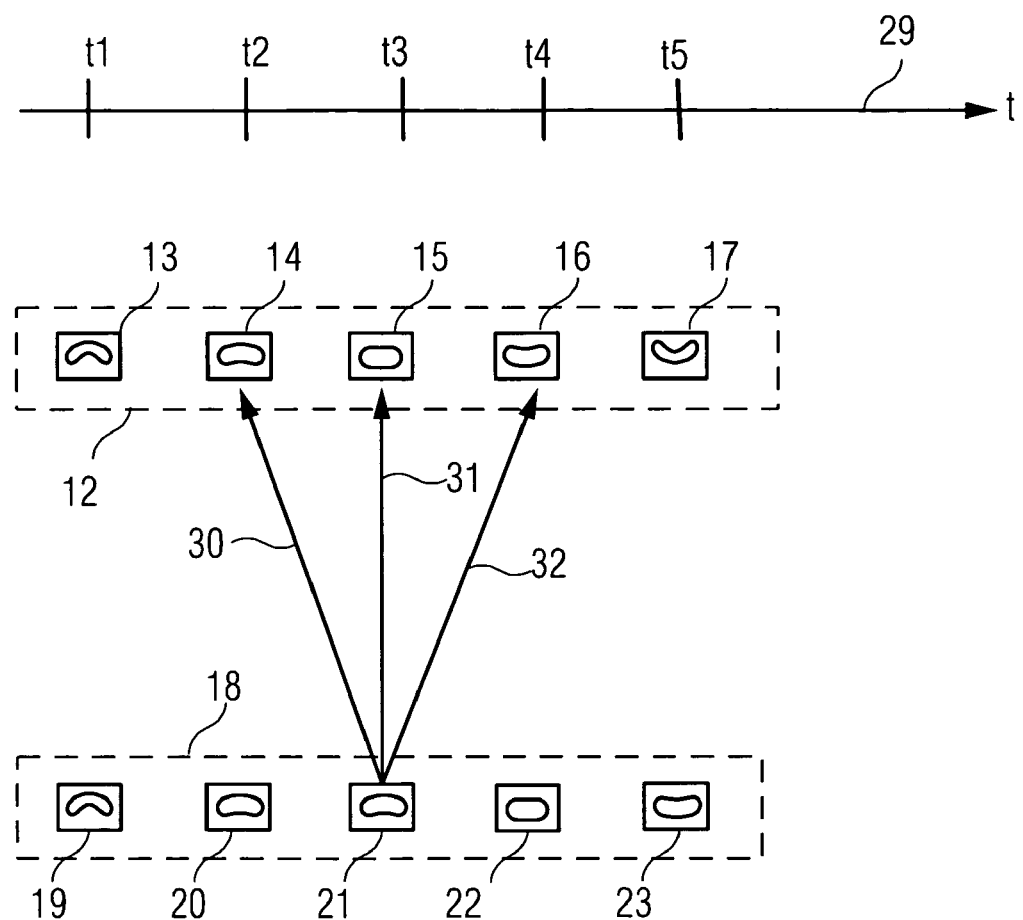
FIG. 2 is a schematic of an inventive method in a second embodiment variant.

FIG. 2 is a schematic of the inventive method in a second embodiment variant. Biosignals are registered in this case, too. They are not, though, used for performing temporal registering but, instead, only limit the time range within which the single images 19-23 in the first image series dataset 12 are used for the comparison with the single images in the second image series dataset 18. The single images 13, 14, 15, 16, and 17 in the first image series dataset 12 are therein three-dimensional CT angiograms of the heart. By means of ECG triggering these can also be assigned to cardiac phases t1, t2, t3, t4, and t5. The single images in the second image series dataset 18 will then be recorded at a later instant. They will be available in the form of 2D angiograms. The single images 13-17 in the first image series dataset 12 are back-projected onto two spatial dimensions in order then to be able to temporally register the single images in the respective image series datasets with one another. The patient's heart rate having changed between recordings, temporal registering by means of the biosignal will no longer tally. This information is not entirely useless, however, but can be used for limiting determining of the maximum similarity of the single images in the second image series dataset 18 to a specific range of the single images in the first image series dataset 12. The single image 21 in the second image series dataset 18 will therefore no longer be examined for maximum similarity along with all single images in the first image series dataset 12, but only with the single images 14, 15, and 16, and the similarities 30-32 obtained therefrom. That is because it is improbable that a single image in the second image series dataset 18 from the middle of the cardiac cycle will tally with a single image in the image series dataset 12 from the beginning or end of the cardiac cycle there. In such an eventuality the heart rate would have had to increase or diminish by a multiple. Such a drastic change in heart rate can, though, be recognized from determining the patient's pulse, and so the time range requiring to be selected from which the images in the first image series dataset 12 are used for the comparison can be narrowed down.

The invention claimed is:

1. A method for temporally registering two image series datasets comprising a plurality of single images for a periodically moving object of a patient, comprising:
   recording a first plurality of single images of a first image series dataset at a first instant;
   recording a second plurality of single images of a second image series dataset at a second instant later than the first instant;
   comparing a similarity of the first plurality of single images and the second plurality of single images;
   determining a specific second single image in the second image series dataset exhibiting a maximum similarity to one of the first single images in the first image series dataset; and
   registering the specific second single image with the one of the first single images,
   wherein the maximum similarity of the single images in the second image series dataset is compared to a specific range of the single images in the first image series dataset due to a change of heart rate of the patient at the first instant and at the second instant.

2. The method as claimed in claim 1, wherein the first image series dataset comprises a first temporal dimension, two or three first spatial dimensions, and a first further dimension depending Eon a first arbitrary recording parameter.

3. The method as claimed in claim 2, wherein the second image series dataset comprises a second temporal dimension, two or three second spatial dimensions, and a second further dimension depending on a second arbitrary recording parameter.

4. The method as claimed in claim 3, wherein a spatially higher-dimensional image series dataset is back-projected onto a spatially lower-dimensional image series dataset.

5. The method as claimed in claim 1, wherein the maximum similarity to each of the single images in the second image series dataset is compared for one or for every single image in the first image series dataset.

6. The method as claimed in claim 1, wherein the maximum similarity to each of the single images in the second image series dataset is compared for one or for every single image in the first image series dataset within a temporally limited range.

7. The method as claimed in claim 1, wherein the maximum similarity is compared based on a distance measure of a distance difference between the first single images and the second single images.

8. The method as claimed in claim 7, wherein the distance measure is calculated by a distance function that measures a distance between pixels or voxels of the first single images and the second single images.

9. The method as claimed in claim 8, wherein the distance function is Euclidean distance.

10. The method as claimed in claim 8, wherein the distance function is Manhattan distance.

11. The method as claimed in claim 8, wherein the distance measure is a sum of all numeric values of the distance function.

12. The method as claimed in claim 8, wherein the distance measure is a root of a sum of squares of all numeric values of the distance function.

13. The method as claimed in claim 1, wherein the maximum similarity is calculated by mutual information.

14. The method as claimed in claim 1, wherein the maximum similarity is calculated with reference to a freely definable image region for determining the maximum similarity.

15. The method as claimed in claim 14, wherein the freely definable image region is defined by an anatomical landmark.

16. The method as claimed in claim 15, wherein the anatomical landmark comprises coronaries or bones of the patient.

17. The method as claimed in claim 14, wherein the freely definable image region is defined by a medical instrument shown in the image region.

* * * * *